(12) United States Patent
Howard et al.

(10) Patent No.: US 9,381,347 B2
(45) Date of Patent: *Jul. 5, 2016

(54) SEGMENTED ELECTRODE LEADS FORMED FROM PRE-ELECTRODES WITH ALIGNMENT FEATURES AND METHODS OF MAKING AND USING THE LEADS

(71) Applicant: Boston Scientific Neuromodulation Corporation, Valencia, CA (US)

(72) Inventors: Joshua Dale Howard, Winnetka, CA (US); Anne Margaret Pianca, Santa Monica, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/841,413

(22) Filed: Aug. 31, 2015

(65) Prior Publication Data

US 2015/0367125 A1    Dec. 24, 2015

Related U.S. Application Data

(63) Continuation of application No. 14/286,829, filed on May 23, 2014, now Pat. No. 9,149,630.

(60) Provisional application No. 61/829,918, filed on May 31, 2013, provisional application No. 61/870,661, filed on Aug. 27, 2013.

(51) Int. Cl.
*A61N 1/00* (2006.01)
*A61N 1/05* (2006.01)
*A61N 1/36* (2006.01)

(52) U.S. Cl.
CPC .............. *A61N 1/0534* (2013.01); *A61N 1/3605* (2013.01); *Y10T 29/49206* (2015.01); *Y10T 29/49208* (2015.01)

(58) Field of Classification Search
CPC ..... A61N 1/0534; A61N 1/05; A61N 1/3605; A61N 1/3752
See application file for complete search history.

(56) References Cited

U.S. PATENT DOCUMENTS

| 4,602,624 A | 7/1986 | Naples et al. |
| 4,630,611 A | 12/1986 | King |

(Continued)

FOREIGN PATENT DOCUMENTS

| EP | 0580928 A1 | 2/1994 |
| EP | 0650694 B1 | 7/1998 |

(Continued)

OTHER PUBLICATIONS

U.S. Appl. No. 14/286,940, filed May 23, 2014.

(Continued)

*Primary Examiner* — Robert N Wieland
(74) *Attorney, Agent, or Firm* — Lowe Graham Jones PLLC; Bruce E. Black

(57) ABSTRACT

A pre-electrode for a stimulation lead includes a generally cylindrical body having an exterior surface, an interior surface, a proximal end, and a distal end. The body includes multiple segmented electrodes disposed along the body; connecting material disposed along the outer surface of the body and coupling each of the segmented electrodes to one another; and multiple cutouts defined between adjacent segmented electrodes. The body also includes one or more of the following 1) a end wall step section formed in the exterior surface of the body on either the distal end or the proximal end of the body; 2) an alignment feature selected from a slot or a notch extending inwardly from the exterior surface of the body, or 3) a longitudinal step section formed in the exterior surface of the body.

20 Claims, 9 Drawing Sheets

(56) References Cited

U.S. PATENT DOCUMENTS

| | | | |
|---|---|---|---|
| 4,744,370 A | 5/1988 | Harris | |
| 5,000,194 A | 3/1991 | van den Honert et al. | |
| 5,135,001 A | 8/1992 | Sinofsky et al. | |
| 5,374,285 A | 12/1994 | Vaiani et al. | |
| 5,458,629 A | 10/1995 | Baudino et al. | |
| 5,522,874 A | 6/1996 | Gates | |
| 5,711,316 A | 1/1998 | Elsberry et al. | |
| 5,713,922 A | 2/1998 | King | |
| 5,800,350 A | 9/1998 | Coppleson et al. | |
| 5,843,148 A | 12/1998 | Gijsbers et al. | |
| 5,938,688 A | 8/1999 | Schiff | |
| 5,987,361 A | 11/1999 | Mortimer | |
| 6,018,684 A | 1/2000 | Bartig et al. | |
| 6,134,478 A | 10/2000 | Spehr | |
| 6,161,047 A | 12/2000 | King et al. | |
| 6,167,311 A | 12/2000 | Rezai | |
| 6,322,559 B1 | 11/2001 | Daulton et al. | |
| 6,510,347 B2 | 1/2003 | Borkan | |
| 6,556,873 B1 | 4/2003 | Smits | |
| 6,564,078 B1 | 5/2003 | Marino et al. | |
| 6,678,564 B2 | 1/2004 | Ketterl et al. | |
| 6,757,970 B1 | 7/2004 | Kuzma et al. | |
| 7,027,852 B2 | 4/2006 | Helland | |
| 7,047,084 B2 | 5/2006 | Erickson et al. | |
| 7,203,548 B2 | 4/2007 | Whitehurst et al. | |
| 7,292,890 B2 | 11/2007 | Whitehurst et al. | |
| 7,489,971 B1 | 2/2009 | Franz | |
| 7,584,005 B1 * | 9/2009 | Jain .................... | A61N 1/0568 607/120 |
| 7,668,601 B2 | 2/2010 | Hegland et al. | |
| 7,761,985 B2 | 7/2010 | Hegland et al. | |
| 7,822,482 B2 | 10/2010 | Gerber | |
| 7,840,188 B2 | 11/2010 | Kurokawa | |
| 7,848,802 B2 | 12/2010 | Goetz | |
| 7,856,707 B2 | 12/2010 | Cole | |
| 7,860,570 B2 | 12/2010 | Whitehurst et al. | |
| 7,974,705 B2 | 7/2011 | Zdeblick et al. | |
| 7,979,140 B2 | 7/2011 | Schulman | |
| 8,000,808 B2 | 8/2011 | Hegland et al. | |
| 8,019,440 B2 | 9/2011 | Kokones et al. | |
| 8,036,755 B2 | 10/2011 | Franz | |
| 8,041,309 B2 | 10/2011 | Kurokawa | |
| 8,099,177 B2 | 1/2012 | Dahlberg | |
| 8,225,504 B2 | 7/2012 | Dye et al. | |
| 8,295,944 B2 | 10/2012 | Howard et al. | |
| 8,321,025 B2 | 11/2012 | Bedenbaugh | |
| 8,359,107 B2 | 1/2013 | Pianca et al. | |
| 8,391,985 B2 | 3/2013 | McDonald | |
| 8,583,237 B2 | 11/2013 | Bedenbaugh | |
| 8,649,873 B2 | 2/2014 | Moffitt et al. | |
| 2001/0023368 A1 | 9/2001 | Black et al. | |
| 2002/0156513 A1 | 10/2002 | Borkan | |
| 2002/0183817 A1 | 12/2002 | Van Venrooij et al. | |
| 2005/0015130 A1 | 1/2005 | Gill | |
| 2005/0038489 A1 | 2/2005 | Grill | |
| 2005/0171587 A1 | 8/2005 | Daglow et al. | |
| 2006/0025841 A1 | 2/2006 | McIntyre | |
| 2006/0247697 A1 | 11/2006 | Sharma et al. | |
| 2007/0168007 A1 | 7/2007 | Kuzma et al. | |
| 2007/0203546 A1 | 8/2007 | Stone et al. | |
| 2007/0219551 A1 | 9/2007 | Honour et al. | |
| 2008/0077186 A1 | 3/2008 | Thompson et al. | |
| 2008/0103580 A1 | 5/2008 | Gerber | |
| 2008/0114230 A1 | 5/2008 | Addis | |
| 2008/0215125 A1 | 9/2008 | Farah et al. | |
| 2008/0255647 A1 | 10/2008 | Jensen et al. | |
| 2009/0054941 A1 | 2/2009 | Eggen et al. | |
| 2009/0204192 A1 | 8/2009 | Carlton et al. | |
| 2010/0030298 A1 | 2/2010 | Martens et al. | |
| 2010/0036468 A1 | 2/2010 | Decre et al. | |
| 2010/0076535 A1 | 3/2010 | Pianca et al. | |
| 2010/0077606 A1 | 4/2010 | Black et al. | |
| 2010/0082076 A1 | 4/2010 | Lee et al. | |
| 2010/0094387 A1 | 4/2010 | Pianca et al. | |
| 2010/0100152 A1 | 4/2010 | Martens et al. | |
| 2010/0268298 A1 | 10/2010 | Moffitt et al. | |
| 2010/0269338 A1 | 10/2010 | Dye | |
| 2010/0269339 A1 | 10/2010 | Dye et al. | |
| 2010/0287770 A1 | 11/2010 | Dadd et al. | |
| 2011/0005069 A1 | 1/2011 | Pianca | |
| 2011/0047795 A1 | 3/2011 | Turner et al. | |
| 2011/0056076 A1 | 3/2011 | Hegland et al. | |
| 2011/0077699 A1 | 3/2011 | Swanson et al. | |
| 2011/0078900 A1 | 4/2011 | Pianca et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0131808 A1 | 6/2011 | Gill | |
| 2011/0238129 A1 | 9/2011 | Moffitt et al. | |
| 2011/0245903 A1 | 10/2011 | Schulte et al. | |
| 2011/0301665 A1 | 12/2011 | Mercanzini et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0203316 A1 | 8/2012 | Moffitt et al. | |
| 2012/0203320 A1 * | 8/2012 | DiGiore ............... | A61N 1/0534 607/148 |
| 2012/0203321 A1 | 8/2012 | Moffitt et al. | |
| 2013/0109254 A1 | 5/2013 | Klardie et al. | |
| 2013/0197424 A1 | 8/2013 | Bedenbaugh | |
| 2013/0197602 A1 | 8/2013 | Pianca et al. | |
| 2013/0261684 A1 | 10/2013 | Howard | |
| 2013/0317587 A1 | 11/2013 | Barker | |
| 2013/0325091 A1 | 12/2013 | Pianca et al. | |
| 2014/0039587 A1 | 2/2014 | Romero | |
| 2014/0039590 A1 | 2/2014 | Moffitt et al. | |
| 2014/0088666 A1 | 3/2014 | Goetz et al. | |
| 2014/0123484 A1 | 5/2014 | DiGiore et al. | |
| 2014/0142671 A1 | 5/2014 | Moffitt et al. | |
| 2014/0155971 A1 | 6/2014 | Pianca et al. | |
| 2014/0180375 A1 | 6/2014 | Pianca et al. | |
| 2015/0151113 A1 | 6/2015 | Govea et al. | |

FOREIGN PATENT DOCUMENTS

| | | |
|---|---|---|
| EP | 0832667 B1 | 2/2004 |
| EP | 1181947 B1 | 1/2006 |
| EP | 2092952 A1 | 8/2009 |
| WO | 9732628 A1 | 9/1997 |
| WO | 9955411 A3 | 2/2000 |
| WO | 00038574 A1 | 7/2000 |
| WO | 0158520 | 8/2001 |
| WO | 02068042 A1 | 9/2002 |
| WO | 2004045707 A1 | 6/2004 |
| WO | 2008018067 | 2/2008 |
| WO | 2008053789 A1 | 5/2008 |
| WO | 2008/100841 | 8/2008 |
| WO | 2009025816 A1 | 2/2009 |
| WO | 2009102536 A1 | 8/2009 |
| WO | 2013162775 | 10/2013 |
| WO | 2014018092 | 1/2014 |

OTHER PUBLICATIONS

U.S. Appl. No. 14/286,889, filed May 23, 2014.
U.S. Appl. No. 14/286,934, filed May 23, 2014.
U.S. Appl. No. 14/325,249, filed Jul. 7, 2014.
U.S. Appl. No. 14/332,212, filed Jul. 15, 2014.
U.S. Appl. No. 14/452,461, filed Aug. 5, 2014.
U.S. Appl. No. 14/286,797, filed May 23, 2014.
U.S. Appl. No. 14/469,214, filed Aug. 26, 2014.
International Search Report and Written Opinion for PCT/US2014/039428 mailed Sep. 26, 2014.
Official Communication for U.S. Appl. No. 14/286,829 mailed Apr. 28, 2015.

* cited by examiner

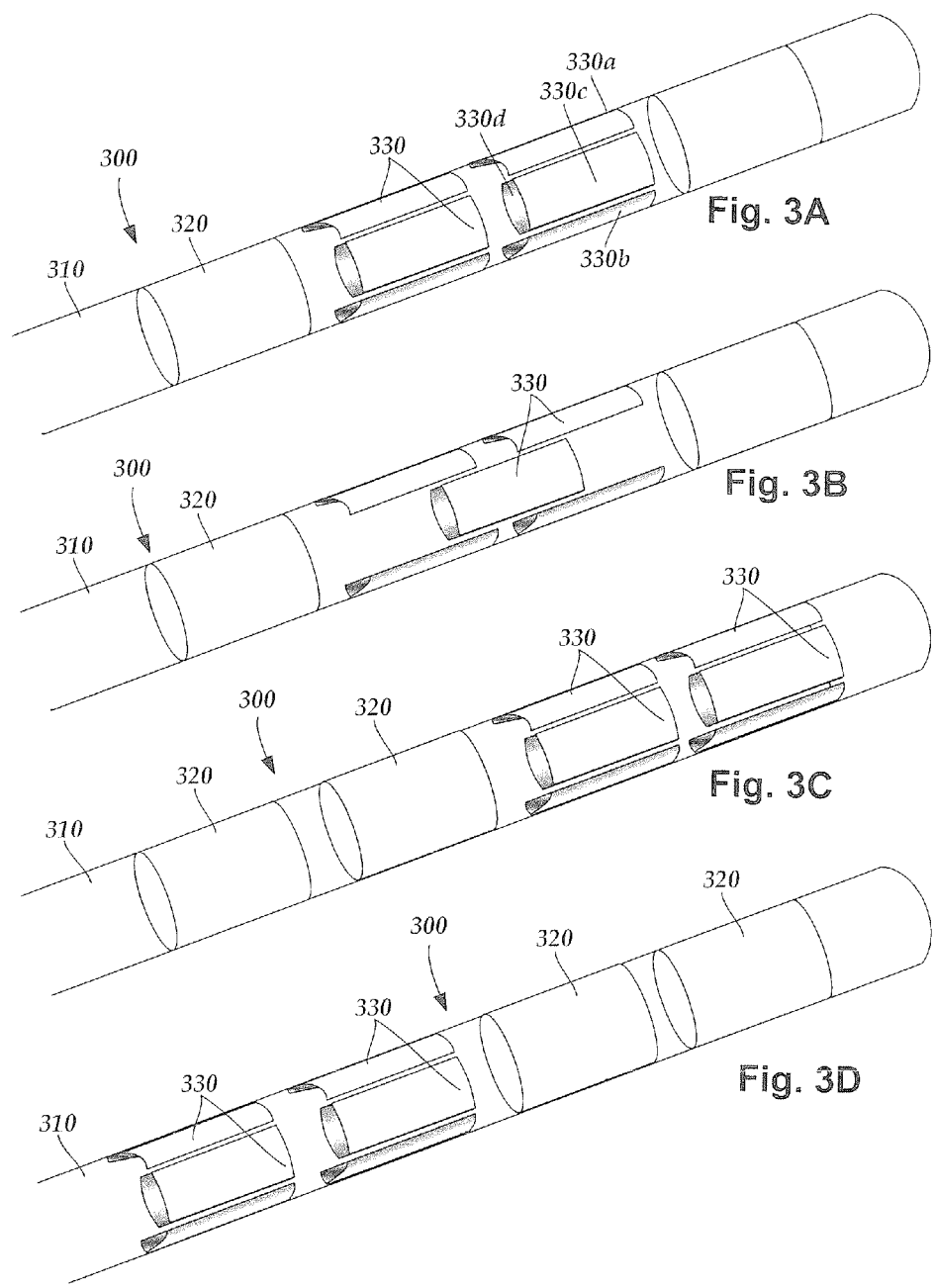

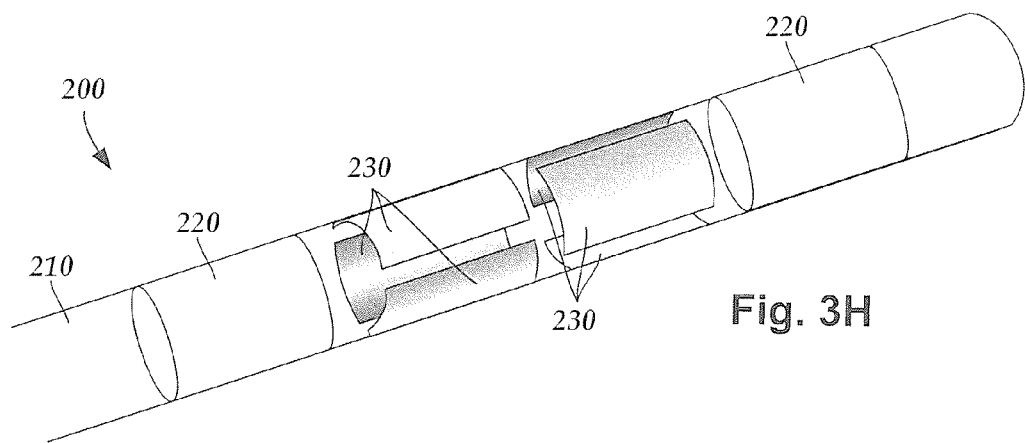
Fig. 3H
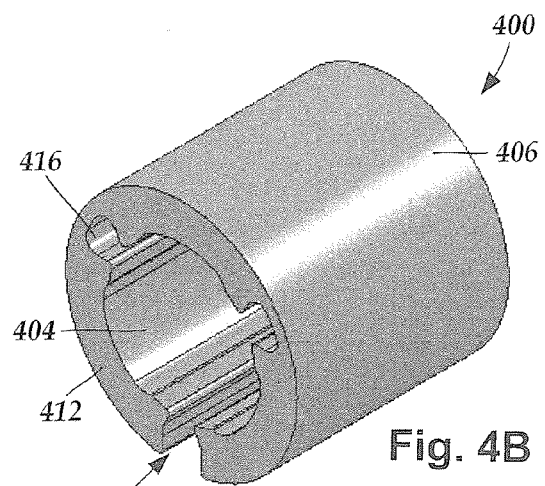
Fig. 4B
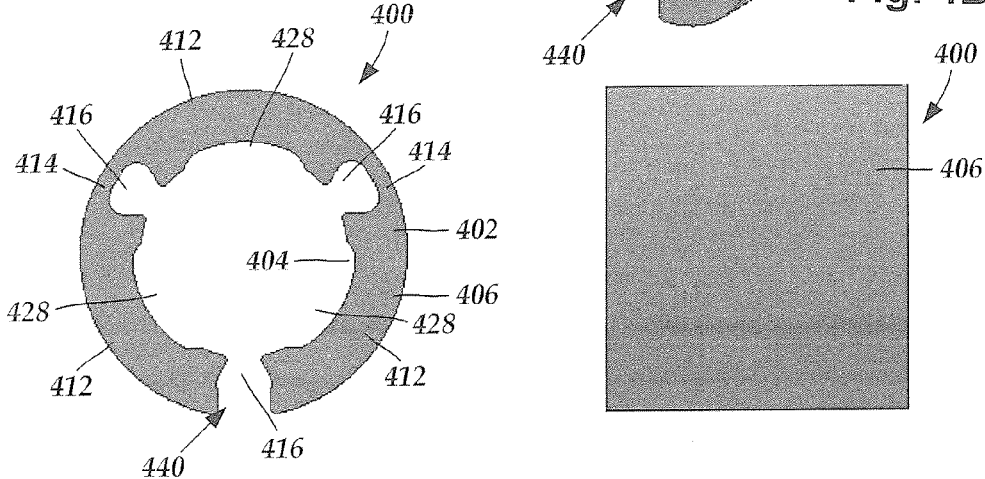
Fig. 4A
Fig. 4C

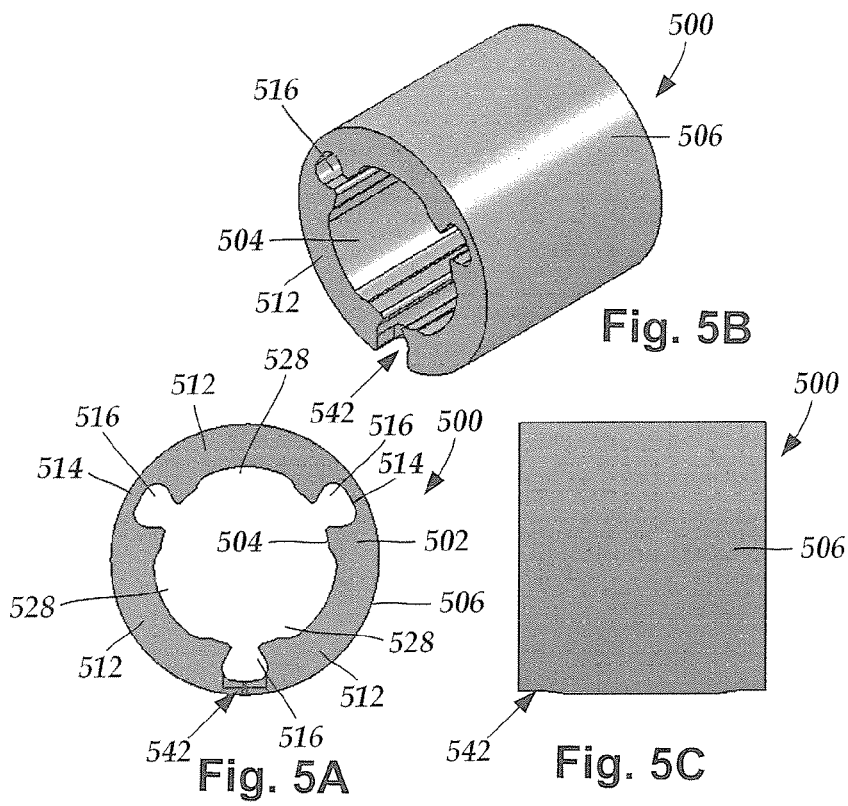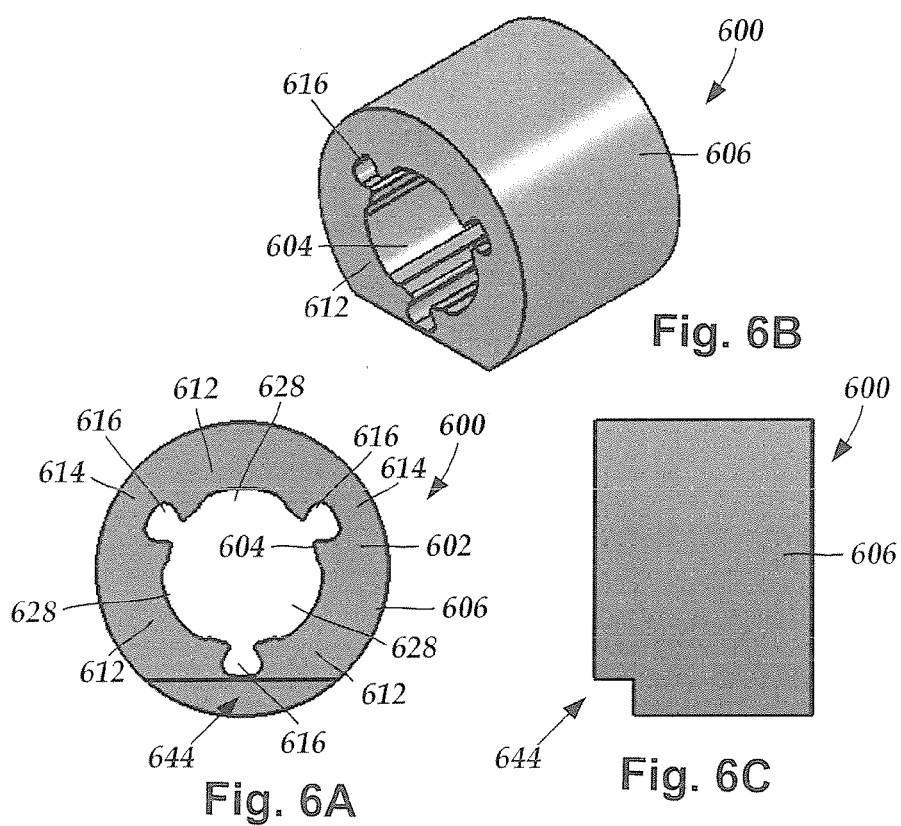

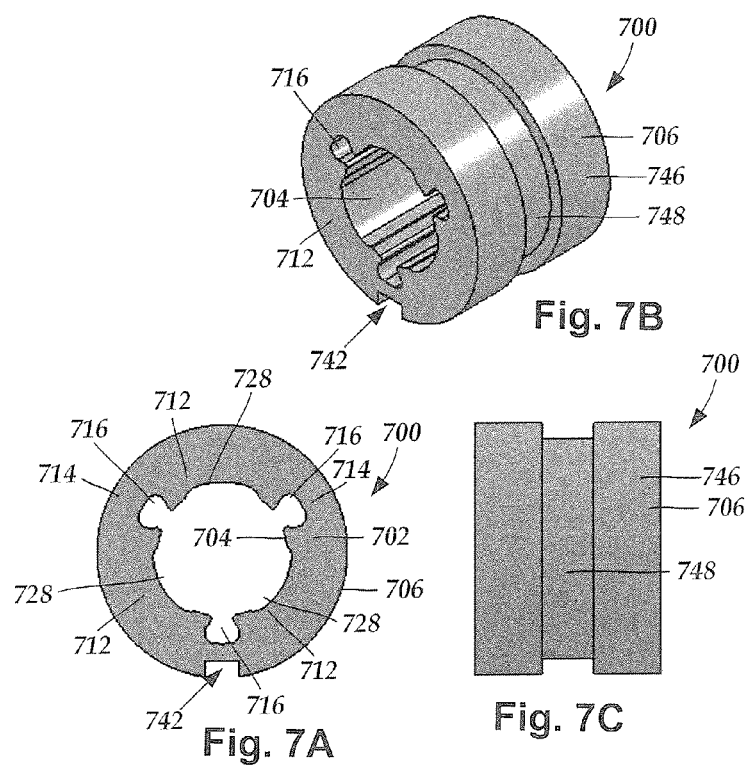
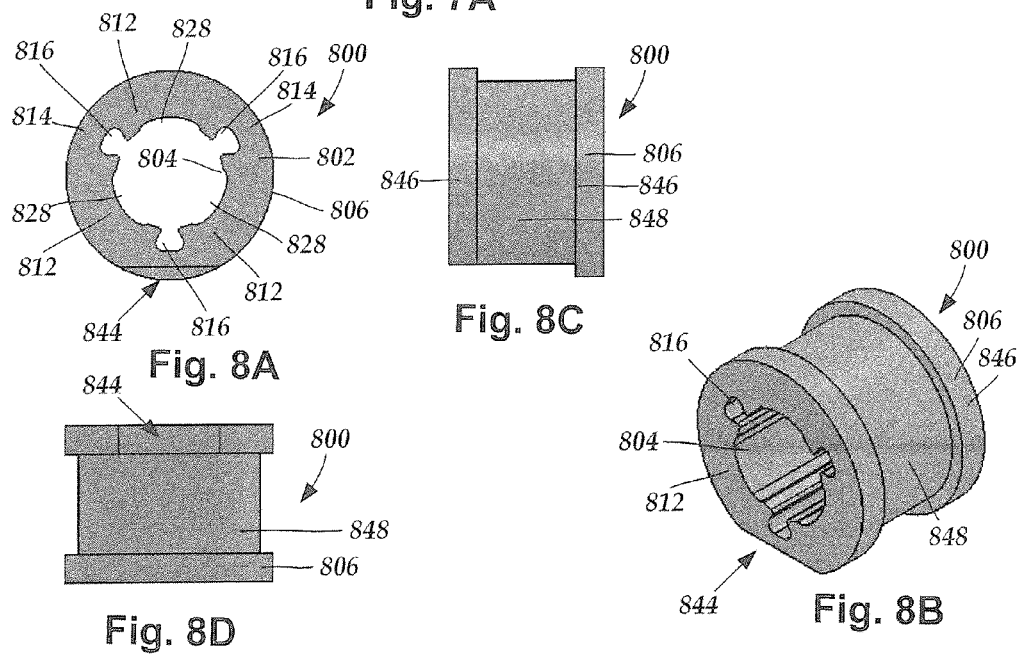

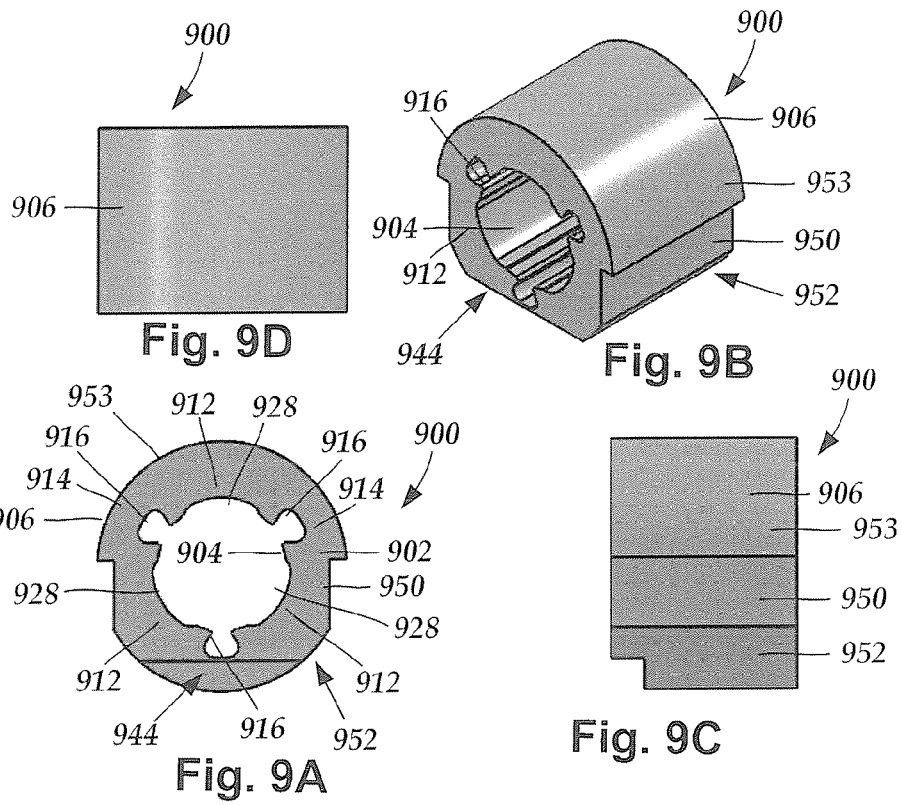
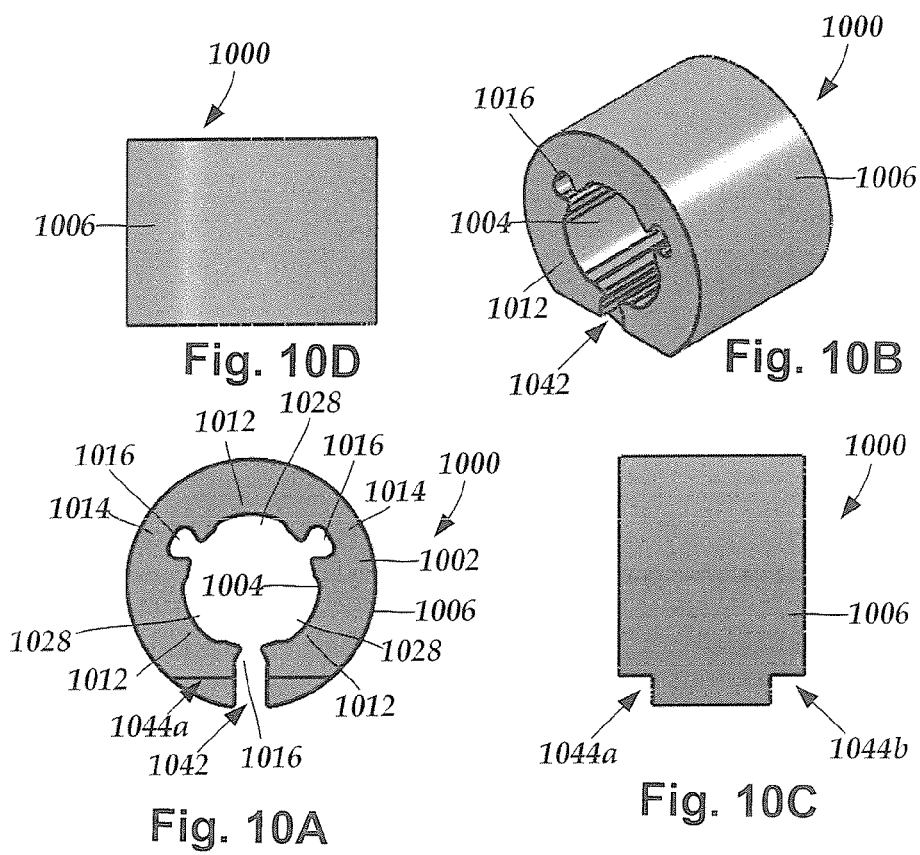

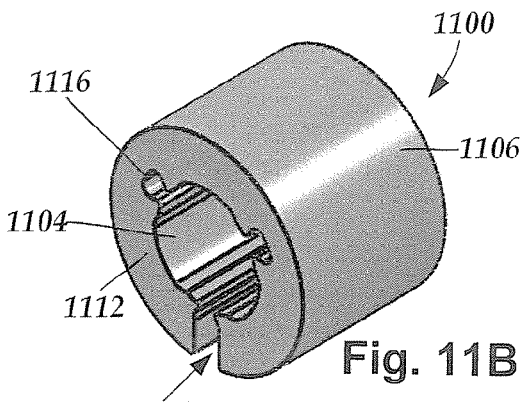
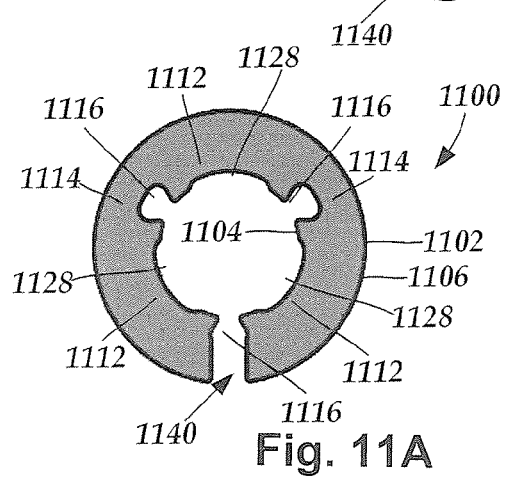
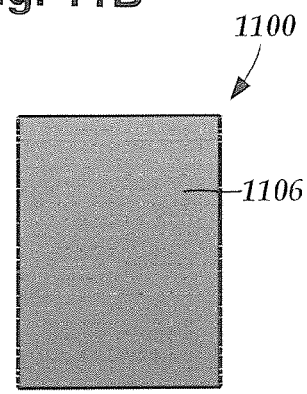
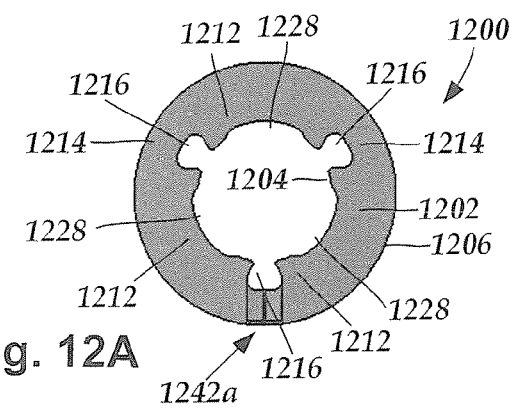
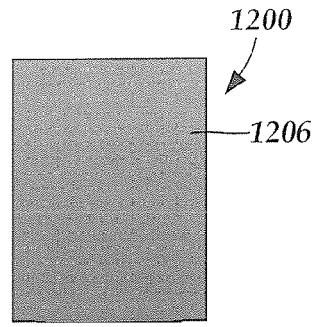
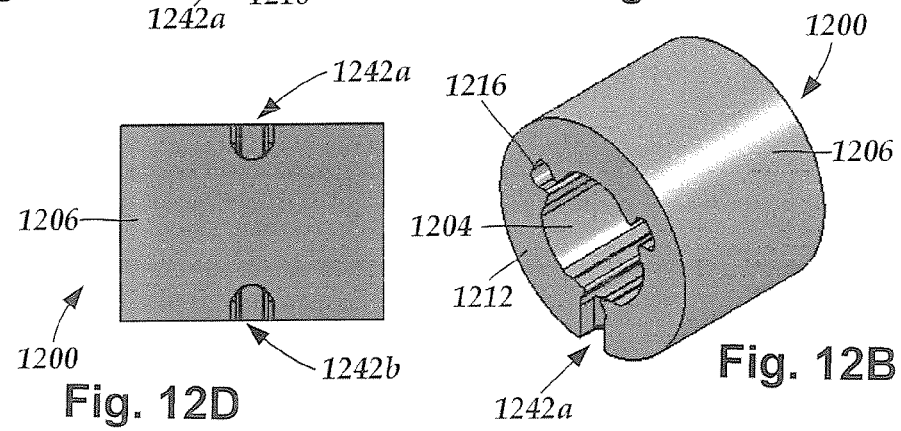
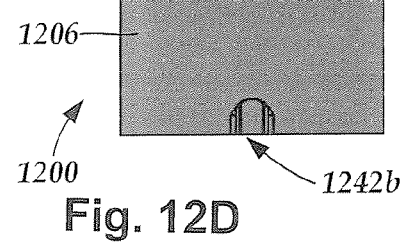

SEGMENTED ELECTRODE LEADS FORMED FROM PRE-ELECTRODES WITH ALIGNMENT FEATURES AND METHODS OF MAKING AND USING THE LEADS

CROSS-REFERENCE TO RELATED APPLICATIONS

This application is a continuation of U.S. patent application Ser. No. 14/286,829 filed May 23, 2014, which issued as U.S. Pat. No. 9,149,630, which claims the benefit under 35 U.S.C. §119(e) of U.S. Provisional Patent Application Ser. No. 61/829,918, filed May 31, 2013, and U.S. Provisional Patent Application Ser. No. 61/870,661, filed Aug. 27, 2013, all of which are incorporated herein by reference.

FIELD

The invention is directed to the area of electrical stimulation systems and leads and methods of making and using the systems and leads. The present invention is also directed to electrical stimulation leads with segmented electrodes formed from pre-electrodes with alignment features, as well as methods of making and using the segmented electrodes, leads, and electrical stimulation systems.

BACKGROUND

Electrical stimulation can be useful for treating a variety of conditions. Deep brain stimulation can be useful for treating, for example, Parkinson's disease, dystonia, essential tremor, chronic pain, Huntington's disease, levodopa-induced dyskinesias and rigidity, bradykinesia, epilepsy and seizures, eating disorders, and mood disorders. Typically, a lead with a stimulating electrode at or near a tip of the lead provides the stimulation to target neurons in the brain. Magnetic resonance imaging ("MRI") or computerized tomography ("CT") scans can provide a starting point for determining where the stimulating electrode should be positioned to provide the desired stimulus to the target neurons.

After the lead is implanted into a patient's brain, electrical stimulus current can be delivered through selected electrodes on the lead to stimulate target neurons in the brain. Typically, the electrodes are formed into rings disposed on a distal portion of the lead. The stimulus current projects from the ring electrodes equally in every direction. Because of the ring shape of these electrodes, the stimulus current cannot be directed to one or more specific positions around the ring electrode (e.g., on one or more sides, or points, around the lead). Consequently, undirected stimulation may result in unwanted stimulation of neighboring neural tissue, potentially resulting in undesired side effects.

BRIEF SUMMARY

One embodiment is a pre-electrode for a stimulation lead that includes a generally cylindrical body having an exterior surface, an interior surface opposite the exterior surface, a proximal end, and a distal end. The body includes multiple segmented electrodes disposed along the body in a spaced-apart configuration with each of the segmented electrodes having opposing side-walls extending between the proximal end and the distal end of the body; connecting material disposed along the outer surface of the body and coupling each of the segmented electrodes to one another; multiple cutouts defined between adjacent segmented electrodes; and at least one end wall step section formed in the exterior surface of the body on either the distal end or the proximal end of the body.

Another embodiment is a pre-electrode for a stimulation lead that includes a generally cylindrical body having an exterior surface, an interior surface opposite the exterior surface, a proximal end, and a distal end. The body includes multiple segmented electrodes disposed along the body in a spaced-apart configuration with each of the segmented electrodes having opposing side-walls extending between the proximal end and the distal end of the body; connecting material disposed along the outer surface of the body and coupling each of the segmented electrodes to one another; multiple cutouts defined between adjacent segmented electrodes; and at least one alignment feature selected from a slot or a notch extending inwardly from the exterior surface of the body and aligned with one of the cutouts.

Yet another embodiment is a pre-electrode for a stimulation lead that includes a generally cylindrical body having an exterior surface, an interior surface opposite the exterior surface, a proximal end, and a distal end. The body includes multiple segmented electrodes disposed along the body in a spaced-apart configuration with each of the segmented electrodes having opposing side-walls extending between the proximal end and the distal end of the body; connecting material disposed along the outer surface of the body and coupling each of the segmented electrodes to one another; multiple cutouts defined between adjacent segmented electrodes; and at least one longitudinal step section formed in the exterior surface of the body along a longitudinal side of the body and extending from the distal end to the proximal end of the body.

A further embodiment is a method of making a stimulation lead. The method includes disposing any of the pre-electrodes described above along a distal end portion of a lead body; forming a lead body around the pre-electrode; and removing the connecting material from the pre-electrode to release the segmented electrodes.

Another embodiment is a lead formed using one or more any of the pre-electrodes described above to generate segmented electrodes during the manufacture of the lead.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 3A is a perspective view of an embodiment of a portion of a lead having a plurality of segmented electrodes, according to the invention;

FIG. 3B is a perspective view of a second embodiment of a portion of a lead having a plurality of segmented electrodes, according to the invention;

FIG. 3C is a perspective view of a third embodiment of a portion of a lead having a plurality of segmented electrodes, according to the invention;

FIG. 3D is a perspective view of a fourth embodiment of a portion of a lead having a plurality of segmented electrodes, according to the invention;

FIG. 3H is a perspective view of an eighth embodiment of a portion of a lead having a plurality of segmented electrodes, according to the invention;

FIG. 4A is a schematic transverse cross-sectional view of one embodiment of a pre-electrode, according to the invention;

FIG. 4B is a schematic perspective view of the pre-electrode of FIG. 4A, according to the invention;

FIG. 4C is a schematic side view of one embodiment of the pre-electrode of FIG. 4A, according to the invention;

FIG. 5A is a schematic transverse cross-sectional view of a second embodiment of a pre-electrode, according to the invention;

FIG. 5B is a schematic perspective view of the pre-electrode of FIG. 5A, according to the invention;

FIG. 5C is a schematic side view of one embodiment of the pre-electrode of FIG. 5A, according to the invention;

FIG. 6A is a schematic transverse cross-sectional view of a third embodiment of a pre-electrode, according to the invention;

FIG. 6B is a schematic perspective view of the pre-electrode of FIG. 6A, according to the invention;

FIG. 6C is a schematic side view of one embodiment of the pre-electrode of FIG. 6A, according to the invention;

FIG. 7A is a schematic transverse cross-sectional view of a fourth embodiment of a pre-electrode, according to the invention;

FIG. 7B is a schematic perspective view of the pre-electrode of FIG. 7A, according to the invention;

FIG. 7C is a schematic side view of one embodiment of the pre-electrode of FIG. 7A, according to the invention;

FIG. 8A is a schematic transverse cross-sectional view of a fifth embodiment of a pre-electrode, according to the invention;

FIG. 8B is a schematic perspective view of the pre-electrode of FIG. 8A, according to the invention;

FIG. 8C is a schematic side view of one embodiment of the pre-electrode of FIG. 8A, according to the invention;

FIG. 8D is a schematic bottom view of one embodiment of the pre-electrode of FIG. 8A, according to the invention;

FIG. 9A is a schematic transverse cross-sectional view of a sixth embodiment of a pre-electrode, according to the invention;

FIG. 9B is a schematic perspective view of the pre-electrode of FIG. 9A, according to the invention;

FIG. 9C is a schematic side view of one embodiment of the pre-electrode of FIG. 9A, according to the invention;

FIG. 9D is a schematic top view of one embodiment of the pre-electrode of FIG. 9A, according to the invention;

FIG. 10A is a schematic transverse cross-sectional view of a seventh embodiment of a pre-electrode, according to the invention;

FIG. 10B is a schematic perspective view of the pre-electrode of FIG. 10A, according to the invention;

FIG. 10C is a schematic side view of one embodiment of the pre-electrode of FIG. 10A, according to the invention;

FIG. 10D is a schematic top view of one embodiment of the pre-electrode of FIG. 10A, according to the invention;

FIG. 11A is a schematic transverse cross-sectional view of a eighth embodiment of a pre-electrode, according to the invention;

FIG. 11B is a schematic perspective view of the pre-electrode of FIG. 11A, according to the invention;

FIG. 11C is a schematic side view of one embodiment of the pre-electrode of FIG. 11A, according to the invention;

FIG. 12A is a schematic transverse cross-sectional view of a ninth embodiment of a pre-electrode, according to the invention;

FIG. 12B is a schematic perspective view of the pre-electrode of FIG. 12A, according to the invention;

FIG. 12C is a schematic side view of one embodiment of the pre-electrode of FIG. 12A, according to the invention; and FIG. 12D is a schematic bottom view of one embodiment of the pre-electrode of FIG. 12A, according to the invention.

DETAILED DESCRIPTION

The invention is directed to the area of electrical stimulation systems and leads and methods of making and using the systems and leads. The present invention is also directed to electrical stimulation leads with segmented electrodes formed from pre-electrodes with alignment features, as well as methods of making and using the segmented electrodes, leads, and electrical stimulation systems.

A lead for deep brain stimulation can include stimulation electrodes, recording electrodes, or a combination of both. At least some of the stimulation electrodes, recording electrodes, or both are provided in the form of segmented electrodes that extend only partially around the circumference of the lead. These segmented electrodes can be provided in sets of electrodes, with each set having electrodes radially distributed about the lead at a particular longitudinal position. For illustrative purposes, the leads are described herein relative to use for deep brain stimulation, but it will be understood that any of the leads can be used for applications other than deep brain stimulation, including spinal cord stimulation, peripheral nerve stimulation, or stimulation of other nerves and tissues.

Suitable implantable electrical stimulation systems include, but are not limited to, a least one lead with one or more electrodes disposed on a distal end of the lead and one or more terminals disposed on one or more proximal ends of the lead. Leads include, for example, percutaneous leads. Examples of electrical stimulation systems with leads are found in, for example, U.S. Pat. Nos. 6,181,969; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,175,710; 8,224,450; 8,271,094; 8,295,944; 8,364,278; 8,391,985; and 8,688,235; and U.S. Patent Application Publication Nos. 2007/0150036; 2009/0187222; 2009/0276021; 2010/0076535; 2010/0268298; 2011/0005069; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; and 2013/0197602, all of which are incorporated by reference.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead can include both recording electrodes and stimulation electrodes or electrodes can be used for both recording and stimulation.

Figure 1:
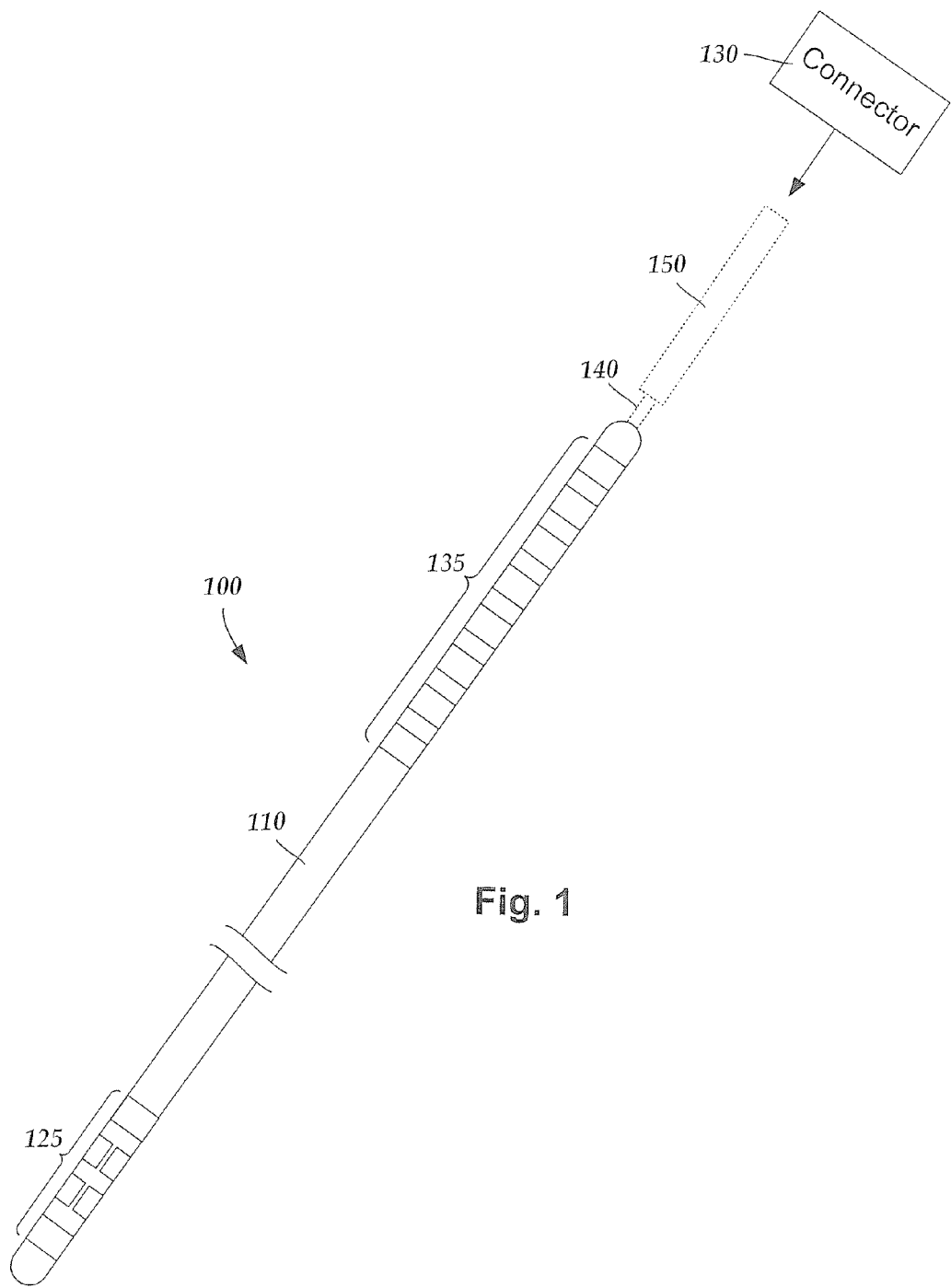
FIG. 1 is a schematic side view of one embodiment of a device for brain stimulation, according to the invention.

FIG. 1 illustrates one embodiment of a device 100 for brain stimulation. The device includes a lead 110, a plurality of electrodes 125 disposed at least partially about a circumference of the lead 110, a plurality of terminals 135, a connector 132 for connection of the electrodes to a control unit, and a stylet 140 for assisting in insertion and positioning of the lead in the patient's brain. The stylet 140 can be made of a rigid material. Examples of suitable materials for the stylet include, but are not limited to, tungsten, stainless steel, and plastic. The stylet 140 may have a handle 150 to assist insertion into the lead 110, as well as rotation of the stylet 140 and lead 110. The connector 132 fits over a proximal end of the lead 110, preferably after removal of the stylet 140.

The control unit (not shown) is typically an implantable pulse generator that can be implanted into a patient's body, for example, below the patient's clavicle area. The pulse generator can have eight stimulation channels which may be independently programmable to control the magnitude of the current stimulus from each channel. In some cases the pulse generator can have more or fewer than eight stimulation channels (e.g., 4-, 6-, 16-, 32-, or more stimulation channels). The control unit can have one, two, three, four, or more connector ports, for receiving the plurality of terminals 135 at the proximal end of the lead 110.

In one example of operation, access to the desired position in the brain can be accomplished by drilling a hole in the patient's skull or cranium with a cranial drill (commonly referred to as a burr), and coagulating and incising the dura mater, or brain covering. The lead 110 can be inserted into the cranium and brain tissue with the assistance of the stylet 140. The lead 110 can be guided to the target location within the brain using, for example, a stereotactic frame and a microdrive motor system. In some embodiments, the microdrive motor system can be fully or partially automatic. The microdrive motor system may be configured to perform one or more the following actions (alone or in combination): insert the lead 110, retract the lead 110, or rotate the lead 110.

In some embodiments, measurement devices coupled to the muscles or other tissues stimulated by the target neurons, or a unit responsive to the patient or clinician, can be coupled to the control unit or microdrive motor system. The measurement device, user, or clinician can indicate a response by the target muscles or other tissues to the stimulation or recording electrode(s) to further identify the target neurons and facilitate positioning of the stimulation electrode(s). For example, if the target neurons are directed to a muscle experiencing tremors, a measurement device can be used to observe the muscle and indicate changes in tremor frequency or amplitude in response to stimulation of neurons. Alternatively, the patient or clinician can observe the muscle and provide feedback.

The lead 110 for deep brain stimulation can include stimulation electrodes, recording electrodes, or both. In at least some embodiments, the lead 110 is rotatable so that the stimulation electrodes can be aligned with the target neurons after the neurons have been located using the recording electrodes.

Stimulation electrodes may be disposed on the circumference of the lead 110 to stimulate the target neurons. Stimulation electrodes may be ring-shaped so that current projects from each electrode equally in every direction from the position of the electrode along a length of the lead 10. Ring electrodes typically do not enable stimulus current to be directed from only a limited angular range around of the lead. Segmented electrodes, however, can be used to direct stimulus current to a selected angular range around the lead. When segmented electrodes are used in conjunction with an implantable pulse generator that delivers constant current stimulus, current steering can be achieved to more precisely deliver the stimulus to a position around an axis of the lead (i.e., radial positioning around the axis of the lead).

To achieve current steering, segmented electrodes can be utilized in addition to, or as an alternative to, ring electrodes. Though the following description discusses stimulation electrodes, it will be understood that all configurations of the stimulation electrodes discussed may be utilized in arranging recording electrodes as well.

The lead 100 includes a lead body 110, one or more optional ring electrodes 120, and a plurality of sets of segmented electrodes 130. The lead body 110 can be formed of a biocompatible, non-conducting material such as, for example, a polymeric material. Suitable polymeric materials include, but are not limited to, silicone, polyurethane, polyurea, polyurethane-urea, polyethylene, or the like. Once implanted in the body, the lead 100 may be in contact with body tissue for extended periods of time. In at least some embodiments, the lead 100 has a cross-sectional diameter of no more than 1.5 mm and may be in the range of 0.5 to 1.5 mm. In at least some embodiments, the lead 100 has a length of at least 10 cm and the length of the lead 100 may be in the range of 10 to 70 cm.

The electrodes can be made using a metal, alloy, conductive oxide, or any other suitable conductive biocompatible material. Examples of suitable materials include, but are not limited to, platinum, platinum iridium alloy, iridium, titanium, tungsten, palladium, palladium rhodium, or the like. Preferably, the electrodes are made of a material that is biocompatible and does not substantially corrode under expected operating conditions in the operating environment for the expected duration of use.

Each of the electrodes can either be used or unused (OFF). When the electrode is used, the electrode can be used as an anode or cathode and carry anodic or cathodic current. In some instances, an electrode might be an anode for a period of time and a cathode for a period of time.

Stimulation electrodes in the form of ring electrodes 120 can be disposed on any part of the lead body 110, usually near a distal end of the lead 100. In FIG. 1, the lead 100 includes two ring electrodes 120. Any number of ring electrodes 120 can be disposed along the length of the lead body 110 including, for example, one, two three, four, five, six, seven, eight, nine, ten, eleven, twelve, thirteen, fourteen, fifteen, sixteen or more ring electrodes 120. It will be understood that any number of ring electrodes can be disposed along the length of the lead body 110. In some embodiments, the ring electrodes 120 are substantially cylindrical and wrap around the entire circumference of the lead body 110. In some embodiments, the outer diameters of the ring electrodes 120 are substantially equal to the outer diameter of the lead body 110. The length of the ring electrodes 120 may vary according to the desired treatment and the location of the target neurons. In some embodiments the length of the ring electrodes 120 are less than or equal to the diameters of the ring electrodes 120. In other embodiments, the lengths of the ring electrodes 120 are greater than the diameters of the ring electrodes 120. The distal-most ring electrode 120 may be a tip electrode (see. e.g., tip electrode 320a of FIG. 3E) which covers most, or all, of the distal tip of the lead.

Deep brain stimulation leads may include one or more sets of segmented electrodes. Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a radially segmented electrode array ("RSEA"), current steering can be performed not only along a length of the lead but also around a circumference of the lead. This provides precise three-dimensional targeting and delivery of the current stimulus to neural target tissue, while potentially avoiding stimulation of other tissue. Examples of leads with segmented electrodes include U.S. Patent Application Publication Nos. 2010/0268298; 2011/0005069; 2011/0130803; 2011/0130816; 2011/0130817; 2011/0130818; 2011/0078900; 2011/0238129; 2012/0016378; 2012/0046710; 2012/0071949; 2012/0165911; 2012/197375; 2012/0203316; 2012/0203320; 2012/0203321, all of which are incorporated herein by reference.

The lead 100 is shown having a plurality of segmented electrodes 130. Any number of segmented electrodes 130 may be disposed on the lead body 110 including, for example, one, two three, four, five, six, seven, eight, nine, ten, eleven, twelve, thirteen, fourteen, fifteen, sixteen or more segmented electrodes 130. It will be understood that any number of segmented electrodes 130 may be disposed along the length of the lead body 110. A segmented electrode 130 typically extends only 75%, 67%, 60%, 50%, 40%, 33%, 25%, 20%, 17%, 15%, or less around the circumference of the lead.

The segmented electrodes 130 may be grouped into sets of segmented electrodes, where each set is disposed around a circumference of the lead 100 at a particular longitudinal portion of the lead 100. The lead 100 may have any number segmented electrodes 130 in a given set of segmented electrodes. The lead 100 may have one, two, three, four, five, six, seven, eight, or more segmented electrodes 130 in a given set. In at least some embodiments, each set of segmented electrodes 130 of the lead 100 contains the same number of segmented electrodes 130. The segmented electrodes 130 disposed on the lead 100 may include a different number of electrodes than at least one other set of segmented electrodes 130 disposed on the lead 100.

The segmented electrodes 130 may vary in size and shape. In some embodiments, the segmented electrodes 130 are all of the same size, shape, diameter, width or area or any combination thereof. In some embodiments, the segmented electrodes 130 of each circumferential set (or even all segmented electrodes disposed on the lead 100) may be identical in size and shape.

Each set of segmented electrodes 130 may be disposed around the circumference of the lead body 110 to form a substantially cylindrical shape around the lead body 110. The spacing between individual electrodes of a given set of the segmented electrodes may be the same, or different from, the spacing between individual electrodes of another set of segmented electrodes on the lead 100. In at least some embodiments, equal spaces, gaps or cutouts are disposed between each segmented electrode 130 around the circumference of the lead body 110. In other embodiments, the spaces, gaps or cutouts between the segmented electrodes 130 may differ in size or shape. In other embodiments, the spaces, gaps, or cutouts between segmented electrodes 130 may be uniform for a particular set of the segmented electrodes 130, or for all sets of the segmented electrodes 130. The sets of segmented electrodes 130 may be positioned in irregular or regular intervals along a length the lead body 110.

Conductor wires that attach to the ring electrodes 120 or segmented electrodes 130 extend along the lead body 110. These conductor wires may extend through the material of the lead 100 or along one or more lumens defined by the lead 100, or both. The conductor wires are presented at a connector (via terminals) for coupling of the electrodes 120, 130 to a control unit (not shown).

When the lead 100 includes both ring electrodes 120 and segmented electrodes 130, the ring electrodes 120 and the segmented electrodes 130 may be arranged in any suitable configuration. For example, when the lead 100 includes two ring electrodes 120 and two sets of segmented electrodes 130, the ring electrodes 120 can flank the two sets of segmented electrodes 130 (see e.g., FIGS. 1, 3A, and 3E-3H). Alternately, the two sets of ring electrodes 120 can be disposed proximal to the two sets of segmented electrodes 130 (see e.g., FIG. 3C), or the two sets of ring electrodes 120 can be disposed distal to the two sets of segmented electrodes 130 (see e.g., FIG. 3D). One of the ring electrodes can be a tip electrode (see, tip electrode 320a of FIGS. 3E and 3G). It will be understood that other configurations are possible as well (e.g., alternating ring and segmented electrodes, or the like).

By varying the location of the segmented electrodes 130, different coverage of the target neurons may be selected. For example, the electrode arrangement of FIG. 3C may be useful if the physician anticipates that the neural target will be closer to a distal tip of the lead body 110, while the electrode arrangement of FIG. 3D may be useful if the physician anticipates that the neural target will be closer to a proximal end of the lead body 110.

Figure 3E:
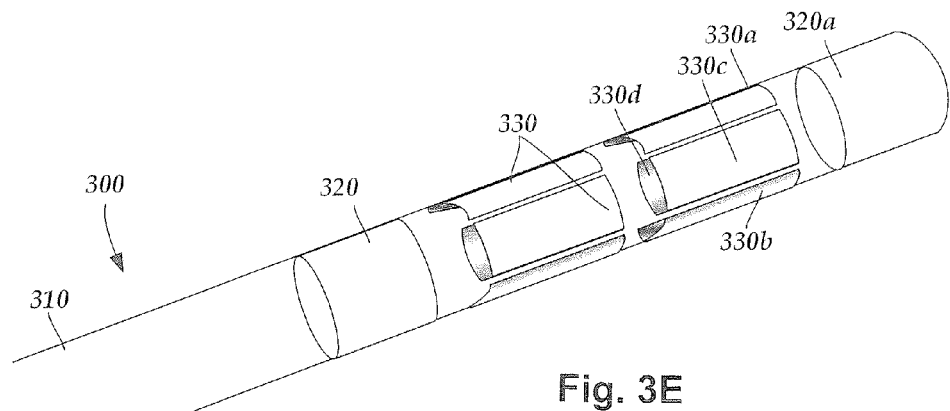
FIG. 3E is a perspective view of a fifth embodiment of a portion of a lead having a plurality of segmented electrodes, according to the invention.
Figure 3F:
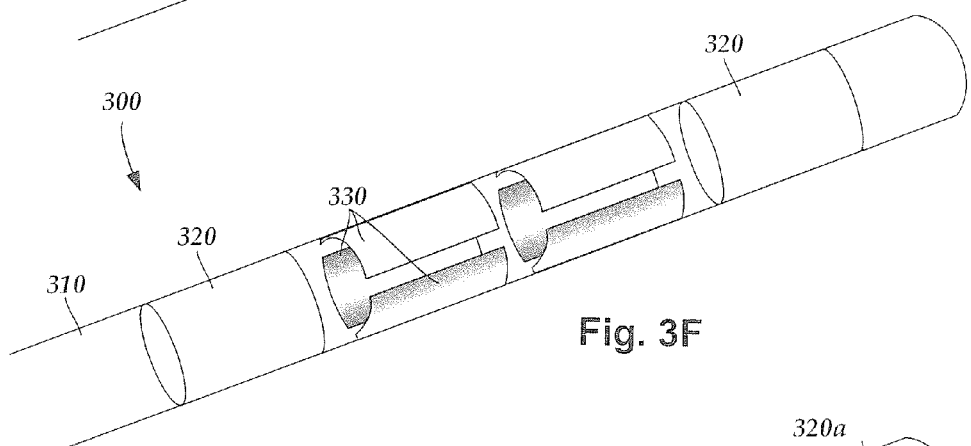
FIG. 3F is a perspective view of a sixth embodiment of a portion of a lead having a plurality of segmented electrodes, according to the invention.
Figure 3G:
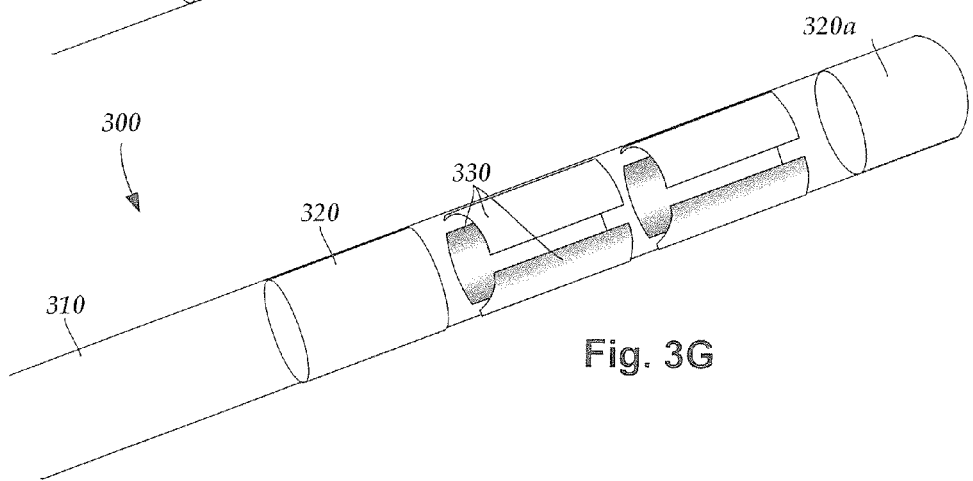
FIG. 3G is a perspective view of a seventh embodiment of a portion of a lead having a plurality of segmented electrodes, according to the invention.

Any combination of ring electrodes 120 and segmented electrodes 130 may be disposed on the lead 100. For example, the lead may include a first ring electrode 120, two sets of segmented electrodes; each set formed of four segmented electrodes 130, and a final ring electrode 120 at the end of the lead. This configuration may simply be referred to as a 1-4-4-1 configuration (FIGS. 3A and 3E). It may be useful to refer to the electrodes with this shorthand notation. Thus, the embodiment of FIG. 3C may be referred to as a 1-1-4-4 configuration, while the embodiment of FIG. 3D may be referred to as a 4-4-1-1 configuration. The embodiments of FIGS. 3F, 3G, and 3H can be referred to as a 1-3-3-1 configuration. Other electrode configurations include, for example, a 2-2-2-2 configuration, where four sets of segmented electrodes are disposed on the lead, and a 4-4 configuration, where two sets of segmented electrodes, each having four segmented electrodes 130 are disposed on the lead. The 1-3-3-1 electrode configuration of FIGS. 3F, 3G, and 3H has two sets of segmented electrodes, each set containing three electrodes disposed around the circumference of the lead, flanked by two ring electrodes (FIGS. 3F and 3H) or a ring electrode and a tip electrode (FIG. 3G). In some embodiments, the lead includes 16 electrodes. Possible configurations for a 16-electrode lead include, but are not limited to 4-4-4-4; 8-8; 3-3-3-3-3-1 (and all rearrangements of this configuration); and 2-2-2-2-2-2-2-2.

Figure 2:
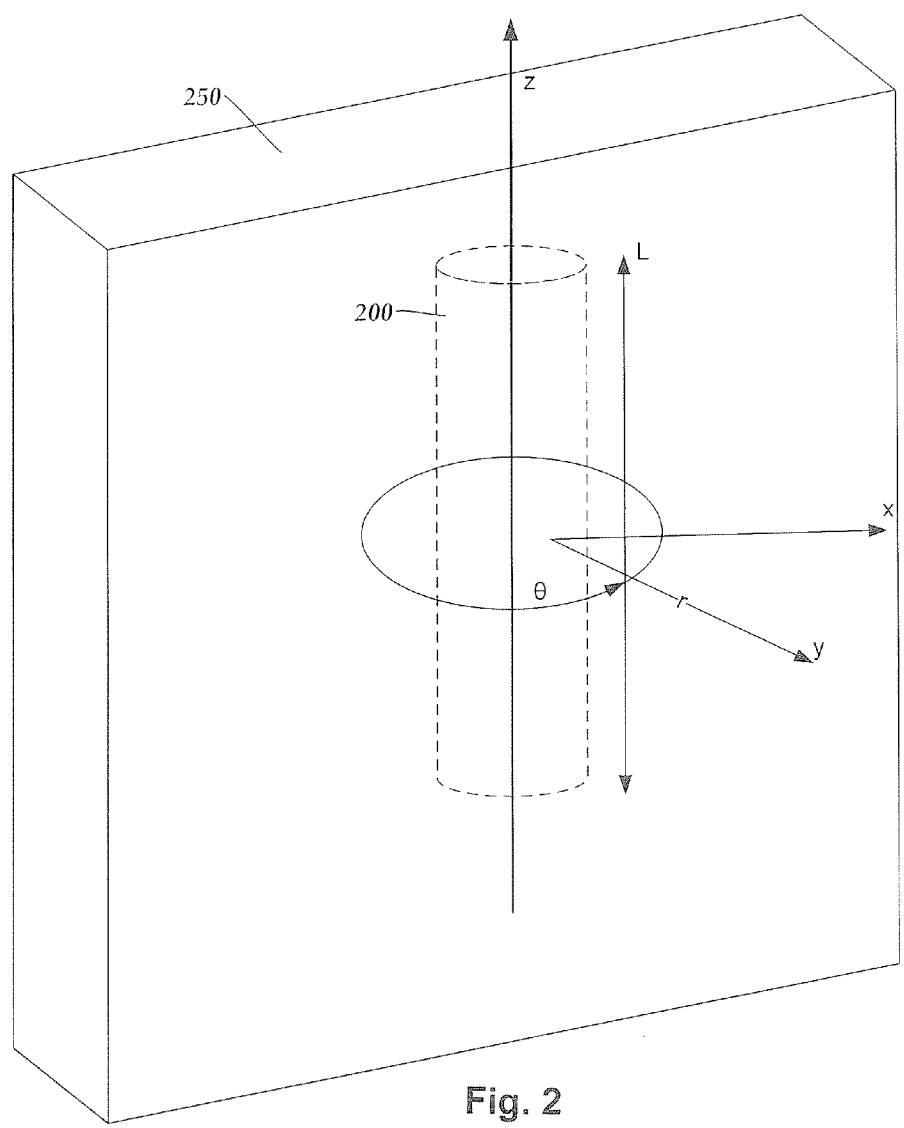
FIG. 2 is a schematic diagram of radial current steering along various electrode levels along the length of a lead, according to the invention.

FIG. 2 is a schematic diagram to illustrate radial current steering along various electrode levels along the length of the lead 200. While conventional lead configurations with ring electrodes are only able to steer current along the length of the lead (the z-axis), the segmented electrode configuration is capable of steering current in the x-axis, y-axis as well as the z-axis. Thus, the centroid of stimulation may be steered in any direction in the three-dimensional space surrounding the lead 200. In some embodiments, the radial distance, r, and the angle θ around the circumference of the lead 200 may be dictated by the percentage of anodic current (recognizing that stimulation predominantly occurs near the cathode, although strong anodes may cause stimulation as well) introduced to each electrode. In at least some embodiments, the configuration of anodes and cathodes along the segmented electrodes allows the centroid of stimulation to be shifted to a variety of different locations along the lead 200.

As can be appreciated from FIG. 2, the centroid of stimulation can be shifted at each level along the length of the lead 200. The use of multiple sets of segmented electrodes at different levels along the length of the lead allows for three-dimensional current steering. In some embodiments, the sets of segmented electrodes are shifted collectively (i.e., the centroid of simulation is similar at each level along the length of the lead). In at least some other embodiments, each set of segmented electrodes is controlled independently. Each set of segmented electrodes may contain two, three, four, five, six, seven, eight or more segmented electrodes. It will be understood that different stimulation profiles may be produced by varying the number of segmented electrodes at each level. For example, when each set of segmented electrodes includes only two segmented electrodes, uniformly distributed gaps (inability to stimulate selectively) may be formed in the stimulation profile. In some embodiments, at least three segmented electrodes 230 in a set are utilized to allow for true 360° selectivity.

As previously indicated, the foregoing configurations may also be used while utilizing recording electrodes. In some embodiments, measurement devices coupled to the muscles or other tissues stimulated by the target neurons or a unit responsive to the patient or clinician can be coupled to the control unit or microdrive motor system. The measurement device, user, or clinician can indicate a response by the target muscles or other tissues to the stimulation or recording electrodes to further identify the target neurons and facilitate positioning of the stimulation electrodes. For example, if the target neurons are directed to a muscle experiencing tremors, a measurement device can be used to observe the muscle and indicate changes in tremor frequency or amplitude in response to stimulation of neurons. Alternatively, the patient or clinician may observe the muscle and provide feedback.

The reliability and durability of the lead will depend heavily on the design and method of manufacture. Fabrication techniques discussed below provide methods that can produce manufacturable and reliable leads.

Returning to FIG. 1, when the lead 100 includes a plurality of sets of segmented electrodes 130, it may be desirable to form the lead 100 such that corresponding electrodes of different sets of segmented electrodes 130 are radially aligned with one another along the length of the lead 100 (see e.g., the segmented electrodes 130 shown in FIG. 1). Radial alignment between corresponding electrodes of different sets of segmented electrodes 130 along the length of the lead 100 may reduce uncertainty as to the location or orientation between corresponding segmented electrodes of different sets of segmented electrodes. Accordingly, it may be beneficial to form electrode arrays such that corresponding electrodes of different sets of segmented electrodes along the length of the lead 100 are radially aligned with one another and do not radially shift in relation to one another during manufacturing of the lead 100.

In other embodiments, individual electrodes in the two sets of segmented electrodes 130 are staggered (see. FIG. 3B) relative to one another along the length of the lead body 110. In some cases, the staggered positioning of corresponding electrodes of different sets of segmented electrodes along the length of the lead 100 may be designed for a specific application.

Segmented electrodes can be used to tailor the stimulation region so that, instead of stimulating tissue around the circumference of the lead as would be achieved using a ring electrode, the stimulation region can be directionally targeted. In some instances, it is desirable to target a parallelepiped (or slab) region 250 that contains the electrodes of the lead 200, as illustrated in FIG. 2. One arrangement for directing a stimulation field into a parallelepiped region uses segmented electrodes disposed on opposite sides of a lead.

FIGS. 3A-3H illustrate leads 300 with segmented electrodes 330, optional ring electrodes 320 or tip electrodes 320a, and a lead body 310. The sets of segmented electrodes 330 each include either two (FIG. 3B), three (FIGS. 3E-3H), or four (FIGS. 3A, 3C, and 3D) or any other number of segmented electrodes including, for example, three, five, six, or more. The sets of segmented electrodes 330 can be aligned with each other (FIGS. 3A-3G) or staggered (FIG. 3H) Any other suitable arrangements of segmented electrodes can be used. As an example, arrangements in which segmented electrodes are arranged helically with respect to each other. One embodiment includes a double helix.

One challenge to making leads with segmented electrodes is the correct placement of the electrodes, and retention of the desired electrode placement, during the manufacturing process and after manufacture. Segmented electrodes and methods of manufacture can be designed to address these and other issues. For example, U.S. Provisional Patent Application Ser. Nos. 61/356,529; 61/829,908; 61/829,912; and 61/829,918, all of which are incorporated herein by reference, as well as other patent applications cited above, provide some examples of segmented electrodes and method of manufacture.

In at least some embodiments a set of segmented electrodes is produced by providing a pre-electrode that is attached to the lead and contains each of the segmented electrodes coupled together by an outer ring of material that is integral with the segmented electrodes. Once the lead body is formed around the pre-electrode, this outer ring is removed to release and separate the individual segmented electrodes. The pre-electrode may appear like a ring electrode on its exterior. Such a pre-electrode is, however, difficult to align with respect to the desired segmented electrode arrangement. Accordingly, the pre-electrode can include alignment features on its exterior surface to facilitate proper alignment during manufacture so that the segmented electrodes will be in the desired spatial arrangement when the outer ring of material is removed.

Sets of radially-disposed segmented electrodes can be formed from pre-electrodes. FIGS. 4A-12D illustrate embodiments of pre-electrodes and sets of segmented electrodes formed from the pre-electrodes (e.g., by grinding down the pre-electrodes to form electrically isolated segmented electrodes). The pre-electrodes, and segmented electrodes formed therefrom, may be formed of an electrical conductor such as a metal, alloy, conductive oxide, or any other suitable conductive material. In some embodiments, the pre-electrodes are formed of platinum, platinum-iridium, iridium, 616L stainless steel (or any other suitable stainless steel), tantalum, Nitinol, iridium rhodium, or a conductive polymer.

In some embodiments, the pre-electrodes are substantially-cylindrical and have a diameter larger than the desired final diameter of a lead. A lead with a cylindrical cross-sectional profile may be obtained by grinding (e.g., center-less grinding), machining, etching, or ablating outer surfaces of the pre-electrodes. The grinding can also release the individual segmented electrodes. In FIGS. 4A-12D three segmented electrodes are shown formed from each pre-electrode. It will be recognized that other embodiments of pre-electrodes can have two, four, five, six, seven, eight, or more segmented electrodes.

FIGS. 4A-4C illustrate one embodiment of a pre-electrode 400 having a body 402 with an interior surface 404 and an exterior surface 406. FIG. 4A is a transverse cross-sectional view of the pre-electrode. FIG. 4B shows a perspective view of the pre-electrode, and FIG. 4C is a side view of the pre-electrode. The body 404 of the pre-electrode 400 is substantially-cylindrical and has a diameter larger than the desired final diameter of a lead upon which the pre-electrode 400 is disposed.

The body 404 defines a slot 440 in the exterior surface 406 that can be used for aligning the pre-electrode 400 visually or aligning the pre-electrode on a corresponding rail or the like in a mold in which the pre-electrode is placed to form the lead body around the pre-electrode. In the embodiment of FIGS. 4A-4C, the slot 440 extends the entire longitudinal length of the pre-electrode 400. It will be understood, however, that in other embodiments, the slot may only extend along a portion (for example, no more than 75%, 50%, 25%, 15%, or 10%) of the longitudinal length of the pre-electrode 400 or there may be two slots extending from opposing ends of the pre-electrode. In the embodiment of FIGS. 4A-4C, the slot 440 also extends from the exterior surface 406 of the body 402 to the interior surface 404 of the body. It will be understood, however, that in other embodiments, the slot does not necessarily extend all of the way to the interior surface of the body, but may form a groove (see, e.g., FIGS. 7A and 7B) in the exterior surface of the body of the pre-electrode.

The pre-electrode has proximal and distal ends defined by the orientation of the pre-electrode when disposed on a lead. For example, when the pre-electrode is disposed on a lead, the proximal end of the pre-electrode is closest to the proximal end portion of the lead. It will be understood that this orientation of the pre-electrodes, as well as the orientation of the pre-electrodes when disposed on leads, applies to each of the pre-electrodes discussed herein.

The pre-electrode 400 includes individual segmented electrodes 412 joined by connecting material 414. The connecting material 414 can be removed (for example, by grinding, machining, etching, ablating, or otherwise removing the connecting material 414) to leave the separated segmented electrodes 412 when the pre-electrode is in place on the lead.

The pre-electrode 400 defines cutouts 416 between the individual segmented electrodes, which typically define the spacing between the segmented electrodes of a particular set of segmented electrodes. The connecting material 414 may correspond only to the material between the segmented electrodes 412 or may include other portions of the pre-electrode 400 (e.g., an outer ring, or rim, of material that can be ground away to release the underlying segmented electrodes). The cutouts can function as lead-retention features by allowing material, such as material from the lead body (including spacers positioned, for example, between sets of segmented electrodes or between a set of segmented electrodes and a ring electrode) or other material, to be placed, or flowed, into the cutouts. The material within the cutouts can also facilitate maintenance of the positioning and spacing of the segmented electrode.

The cutouts 416 have perimeters extending between adjacent portions of the interior surface 404 of the pre-electrode 400. The perimeter can be continuous or discontinuous. Each cutout abuts two segmented electrodes with portions of the perimeter forming side-walls of those segmented electrodes. In at least some embodiments, the perimeter of at least one of the cutouts is shaped such that one or more open cavities (e.g., nooks, notches, voids, indentations, open spaces, or the like or combinations thereof) are formed along at least a portion of the side-wall of at least one of the segmented electrodes abutting that cutout. The cutouts 416 can have a variety of different shapes and arrangements. Examples of other shapes and arrangements for the cutouts 416 can be found in U.S. Provisional Patent Application Ser. Nos. 61/356,529; 61/829,908; 61/829,912; and 61/829,918, all of which are incorporated by reference.

The pre-electrode 400 further includes one or more channels 428 formed in the segmented electrodes 412. There may be one, two, three, four, or more channels formed in each of the segmented electrodes. The number of channels in each segmented electrode may be the same or different from the number of channels in other segmented electrodes. The channels 428 may be particularly useful for attachment of a conductor to the segmented electrode 412. In at least some embodiments, the one or more channels are defined along the interior surface 404 of the body 402. In FIG. 4A, the one or more channels 428 have arcuate transverse cross-sectional shapes. The channels 428 can have a variety of different shapes and arrangements. Examples of other shapes and arrangements for the channels 428 can be found in U.S. Provisional Patent Application Ser. Nos. 61/356,529; 61/829,908; 61/829,912; and 61/829,918, all of which are incorporated by reference.

FIGS. 5A-5C illustrate another embodiment of a pre-electrode 500 having a body 502 with an interior surface 504 and an exterior surface 506. The pre-electrode 500 also includes segmented electrodes 512 joined by connecting material 514, as well as cutouts 516 and channels 528. All of these elements, and the design considerations for these elements, are the same as the corresponding (similarly named) elements of the embodiment illustrated in FIGS. 4A-4C.

As an alignment feature, pre-electrode 500 defines at least one notch 542 in the exterior surface 506 that can be used for aligning the pre-electrode 500 visually or aligning the pre-electrode on a corresponding protrusion or the like in a mold in which the pre-electrode is placed to form the lead body around the pre-electrode. In the embodiment of FIGS. 5A-5C, the notch 542 extends a relatively short distance along the longitudinal length of the pre-electrode 500. In at least some embodiments, the notch 542 extends at least 5%, 10%, 15%, 20%, or 25% of the longitudinal length of the pre-electrode 500. In some embodiments, there may be two notches (see. e.g., FIG. 12D) extending from opposing ends of the pre-electrode 500. In the embodiment of FIGS. 5A-5C, the notch 542 also extends from the exterior surface 506 of the body 502 to the interior surface 504 of the body. It will be understood, however, that in other embodiments, the notch does not necessarily extend all of the way to the interior surface of the body. Also, in the embodiment of FIGS. 5A-5C, the notch 542 is aligned with one of the cutouts 516. It will be recognized that one or more additional notches could be aligned with one or more of the other cutouts 516 around the circumference of the pre-electrode. If multiple notches are present, the notches may be on the same end (e.g., the proximal end or the distal end) of the pre-electrode or may be distributed in any desired arrangement between both the distal and proximal ends.

FIGS. 6A-6C illustrate a third embodiment of a pre-electrode 600 having a body 602 with an interior surface 604 and an exterior surface 606. The pre-electrode 600 also includes segmented electrodes 612 joined by connecting material 614, as well as cutouts 616 and channels 628. All of these elements, and the design considerations for these elements, are the same as the corresponding (similarly named) elements of the embodiment illustrated in FIGS. 4A-4C.

As an alignment feature, pre-electrode 600 defines at least one end wall step section 644 in the exterior surface 606 that can be used for aligning the pre-electrode 600 visually or aligning the pre-electrode on a corresponding protrusion, shelf, shoulder, platform, or the like in a mold in which the pre-electrode is placed to form the lead body around the pre-electrode. The end wall step section 644 has a shape that appears as if a cylindrical pre-electrode was cut along two intersecting planes to remove a section of the cylinder. It will be understood, however, that actual cutting of the pre-electrode is not required, but merely that the pre-electrode has a shape that could have been obtained by cutting a cylinder along the two intersecting planes. In at least some embodiments, the two intersecting planes are orthogonal to each other, as illustrated, for example, in FIGS. 6A-6C.

An end wall step section 644 can be provided at either the distal end or the proximal end (or at both ends) of the pre-electrode. In at least some embodiments, the radial width of the connecting material 614 is at least as large as the difference between the largest outer radius of the body 602 of the pre-electrode 600 and the smallest outer radius of the end wall step section 644. Such an arrangement can maintain a uniform outer radius of the segmented electrodes 612, if desired. In at least some embodiments, the pre-electrode of FIGS. 6A-6C will have a thicker connecting material 614 than would be used for the pre-electrodes illustrated in FIGS. 4A-4C or 5A-5C. The radii described herein are measured from a central longitudinal axis extending along the pre-electrode and defined as central with relation to the lumen in the pre-electrode or with relation to the final set of segmented electrodes obtained from the pre-electrode. In many embodiments, the central longitudinal axis of the pre-electrode will align with the central longitudinal axis of the lead when the pre-electrode is positioned on the lead.

In the embodiment of FIGS. 6A-6C, the end wall step section 644 extends a distance along the longitudinal length of the pre-electrode 600. In at least some embodiments, the end wall step section 644 extends at least 5%, 10%, 15%, 20%, 25%, 30%, 40%, or 50% of the longitudinal length of the pre-electrode 600. In some embodiments, there may be two end wall step sections 644 extending from opposing ends of the pre-electrode 600. The end wall step section 644 extends inwardly from the exterior surface 606 of the body 602 and may or may not (as illustrated in FIGS. 6A-6C) extend to the interior surface 604 of the body. Also, in the embodiment of FIGS. 6A-6C, the end wall step section 644 is aligned with one of the cutouts 616.

FIGS. 7A-7C illustrate a fourth embodiment of a pre-electrode 700 having a body 702 with an interior surface 704 and an exterior surface 706. The pre-electrode 700 also includes segmented electrodes 712 joined by connecting material 714, as well as cutouts 716 and channels 728. All of these elements, and the design considerations for these elements, are the same as the corresponding (similarly named) elements of the embodiment illustrated in FIGS. 4A-4C.

As an alignment feature, pre-electrode 700 defines at least one notch 742 in the exterior surface 706 that can be used for aligning the pre-electrode 700 visually or aligning the pre-electrode on a corresponding protrusion or the like in a mold in which the pre-electrode is placed to form the lead body around the pre-electrode. In the embodiment of FIGS. 7A-7C, the notch 742 extends a relatively short distance along the longitudinal length of the pre-electrode 700. In at least some embodiments, the notch 742 extends at least 5%, 10%, 15%, 20%, or 25% of the longitudinal length of the pre-electrode 700. In some embodiments, there may be two notches extending from opposing ends of the pre-electrode 700. The notch 742 also extends inwardly from the exterior surface 706 of the body 702. In the embodiment of FIGS. 7A-7C, the notch 742 does not extend completely to the interior surface 704 of the body, but rather forms a longitudinal groove in the exterior surface 706 of the body 702. It will be understood, however, that in other embodiments, the notch does extend all of the way to the interior surface of the body. Also, in the embodiment of FIGS. 7A-7C, the notch 742 is aligned with one of the cutouts 716. It will be recognized that one or more additional notches could be aligned with one or more of the other cutouts 716 around the circumference of the pre-electrode. If multiple notches are present, the notches may be on the same end (e.g., the proximal end or the distal end) of the pre-electrode or may be distributed in any desired arrangement between both the distal and proximal ends.

Pre-electrode 700 also includes an annular groove 748 disposed between two annular lips 746. The annular lips 746 have a larger outer radius (by at least 5%, 10%, 15%, 20%, or more) than the annular groove 748. Providing the annular groove 748 may reduce the amount of material that is removed from the pre-electrode to release the segmented electrodes 712 and may also facilitate welding a conductor to each of the segmented electrodes on the interior surface aligned with the annular group as there is less material to be heated within the annular groove. In at least some embodiments, the annular groove 748 has a width that extends at least 20%, 25%, 30%, 50%, 60%, or 75% of the longitudinal length of the pre-electrode 700.

FIGS. 8A-8D illustrate a fifth embodiment of a pre-electrode 800 having a body 802 with an interior surface 804 and an exterior surface 806. The pre-electrode 800 also includes segmented electrodes 812 joined by connecting material 814, as well as cutouts 816 and channels 828. All of these elements, and the design considerations for these elements, are the same as the corresponding (similarly named) elements of the embodiment illustrated in FIGS. 4A-4C.

As an alignment feature, pre-electrode 800 defines at least one end wall step section 844 which has the same design characteristics and considerations as the end wall step section 744 of the embodiment of FIGS. 7A-7C.

The pre-electrode 800 also includes an annular groove 848 disposed between two annular lips 846 similar to the embodiment of FIGS. 7A-7C. The annular lips 846 have a larger outer radius (by at least 5%, 10%, 15%, 20%, or more) than the annular groove 848. Providing the annular groove 848 may reduce the amount of material that must be removed from the pre-electrode and may also facilitate welding a conductor to each of the segmented electrodes on the interior surface aligned with the annular group as there is less material to be heated within the annular groove. In at least some embodiments, the annular groove 848 has a width that extends at least 20%, 25%, 30%, 50%, 60%, or 75% of the longitudinal length of the pre-electrode 800. In at least some embodiments, a wider annular groove is preferred to provide one or more of the benefits described above.

FIGS. 9A-9D illustrate a sixth embodiment of a pre-electrode 900 having a body 902 with an interior surface 904 and an exterior surface 906. The pre-electrode 900 also includes segmented electrodes 912 joined by connecting material 914, as well as cutouts 916 and channels 928. All of these elements, and the design considerations for these elements, are the same as the corresponding (similarly named) elements of the embodiment illustrated in FIGS. 4A-4C.

As an alignment feature, pre-electrode 900 defines at least one end wall step section 944 which has the same design characteristics and considerations as the end wall step section 744 of the embodiment of FIGS. 7A-7C.

The pre-electrode 900 also defines at least one longitudinal step section 950 in the exterior surface 906 that can be used for aligning the pre-electrode 900 visually or aligning the pre-electrode on a corresponding protrusion, shelf, shoulder, platform, or the like in a mold in which the pre-electrode is placed to form the lead body around the pre-electrode. In the embodiment of FIGS. 9A-9D, the pre-electrode 900 has two longitudinal step sections 950 disposed on opposite longitudinal sides of the pre-electrode. The longitudinal step section 950 has a shape that appears as if the longitudinal side of a cylindrical pre-electrode was cut along a plane to remove a section of the cylinder. It will be understood, however, that actual cutting of the longitudinal side of the pre-electrode is not required, but merely that the pre-electrode has a shape that could have been obtained by cutting a cylinder along an intersecting plane. In at least some embodiments, the plane is parallel to a longitudinal axis of the pre-electrode, as illustrated, for example, in FIGS. 9A-9D. In at least some embodiments, the radial width of the connecting material 914 is at least as large as the difference between the largest outer radius of the body 902 of the pre-electrode 900 and the smallest outer radius of the longitudinal step section 950. Such an arrangement can maintain a uniform outer radius of the segmented electrodes 912, if desired. In at least some embodiments, the pre-electrode of FIGS. 9A-6C will have a thicker connecting material 914 than would be used for the pre-electrodes illustrated in FIGS. 4A-4C or 5A-5C.

Region 952 and region 953 circumferentially flank the longitudinal step section 950. Region 952 (exclusive of the end wall step section 944) of the pre-electrode may have a same outer radius as region 953 or the outer radius of region 952 (exclusive of the end wall step section 944) may be smaller than the outer radius of region 953. The outer radius of region 952 (exclusive of the end wall step section 944) may be uniform or non-uniform FIGS. 10A-10D illustrate a seventh embodiment of a pre-electrode 1000 having a body 1002 with an interior surface 1004 and an exterior surface 1006. The pre-electrode 1000 also includes segmented electrodes 1012 joined by connecting material 1014, as well as cutouts 1016 and channels 1028. All of these elements, and the design considerations for these elements, are the same as the corresponding (similarly named) elements of the embodiment illustrated in FIGS. 4A-4C.

As an alignment feature, pre-electrode 1000 defines two end wall step section 1044a, 1044b with one end wall step section disposed on each of the proximal and distal ends of the pre-electrodes. The two end wall step sections 1044a. 1044b have the same design characteristics and considerations as the end wall step section 744 of the embodiment of FIGS. 7A-7C.

The pre-electrode 1000 also includes at least one notch 1042 on either the distal end or the proximal end or notches on both the distal and proximal ends of the pre-electrode. The notch(es) 1042 extends at least 5%, 10%, 15%, 20%, or 25% of the longitudinal length of the pre-electrode 1000. In the embodiment of FIGS. 10A-10D, the notch 1042 also extends from the exterior surface 1006 of the body 1002 to the interior surface 1004 of the body. It will be understood, however, that in other embodiments, the notch does not necessarily extend all of the way to the interior surface of the body. Also, in the embodiment of FIGS. 10A-10D, the notch 1042 is aligned with one of the cutouts 1016. It will be recognized that one or more additional notches could be aligned with one or more of the other cutouts 1016 around the circumference of the pre-electrode. If multiple notches are present, the notches may be on the same end (e.g., the proximal end or the distal end) of the pre-electrode or may be distributed in any desired arrangement between both the distal and proximal ends.

FIGS. 11A-11C illustrate an eighth embodiment of a pre-electrode 1100 having a body 1102 with an interior surface 1104 and an exterior surface 1106. The pre-electrode 1100 also includes segmented electrodes 1112 joined by connecting material 1114, as well as cutouts 1116 and channels 1128. All of these elements, and the design considerations for these elements, are the same as the corresponding (similarly named) elements of the embodiment illustrated in FIGS. 4A-4C. The connecting material 1114 of pre-electrode 1100 is thicker than the connecting material 414 of pre-electrode 400 of FIGS. 4A-4C As an alignment feature, pre-electrode 1100 defines a slot 1140 in the exterior surface 1106 that can be used for aligning the pre-electrode 1100 visually or aligning the pre-electrode on a corresponding rail or the like in a mold in which the pre-electrode is placed to form the lead body around the pre-electrode. In the embodiment of FIGS. 11A-11C, the slot 1140 extends the entire longitudinal length of the pre-electrode 1100. It will be understood, however, that in other embodiments, the slot may only extend along a portion (for example, no more than 75%, 50%, 25%, 15%, or 10%) of the longitudinal length of the pre-electrode 1100 or there may be two slots extending from opposing ends of the pre-electrode. In the embodiment of FIGS. 11A-11C, the slot 1140 also extends from the exterior surface 1106 of the body 1102 to the interior surface 1104 of the body. It will be understood, however, that in other embodiments, the slot does not necessarily extend all of the way to the interior surface of the body, but may form a groove in the exterior surface of the body of the pre-electrode.

FIGS. 12A-12D illustrate a ninth embodiment of a pre-electrode 1200 having a body 1202 with an interior surface 1204 and an exterior surface 1206. The pre-electrode 1200 also includes segmented electrodes 1212 joined by connecting material 1214, as well as cutouts 1216 and channels 1228. All of these elements, and the design considerations for these elements, are the same as the corresponding (similarly named) elements of the embodiment illustrated in FIGS. 4A-4C.

As an alignment feature, pre-electrode 1200 also two notches 1242a. 1242b on the distal end and the proximal end of the pre-electrode, respectively. The notches 1242a. 1242b each extend at least 5%, 12%, 15%, 20%, or 25% of the longitudinal length of the pre-electrode 1200. In the embodiment of FIGS. 12A-12D, the notches 1242a. 1242b each also extend from the exterior surface 1206 of the body 1202 to the interior surface 1204 of the body. It will be understood, however, that in other embodiments, either, or both, of the notches does not necessarily extend all of the way to the interior surface of the body. Also, in the embodiment of FIGS. 12A-10D, the notches 1242a, 1242b are aligned with one of the cutouts 1216. It will be recognized that one or more additional notches could be aligned with one or more of the other cutouts 1216 around the circumference of the pre-electrode. If multiple notches are present, the notches may be on the same end (e.g., the proximal end or the distal end) of the pre-electrode or may be distributed in any desired arrangement between both the distal and proximal ends.

The embodiments illustrated in FIGS. 4A-12D are examples of pre-electrodes. It will be understood, however, that other pre-electrodes can be formed using any combination of slots, notches, end wall step sections, longitudinal step sections, annular grooves, annular lips, and longitudinal grooves.

The above specification, examples, and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A pre-electrode for a stimulation lead, the pre-electrode comprising:
   a generally cylindrical body comprising an exterior surface, a proximal end, and a distal end, the body comprising
      a plurality of segmented electrodes disposed around the body in a circumferentially spaced-apart configuration, each of the plurality of segmented electrodes having opposing side-walls extending between the proximal end and the distal end of the body,
      connecting material forming at least a portion of the exterior surface of the body and coupling together the plurality of segmented electrodes, and
      at least one end wall step section formed in the exterior surface of the body on either the distal end or the proximal end of the body, wherein the at least one end wall step section extends through at least some of the connecting material that is located between at least two circumferentially-adjacent segmented electrodes.

2. The pre-electrode of claim 1, wherein the at least one end wall step section has an appearance of a section, bounded by two intersection planes, removed from the generally cylindrical body.

3. The pre-electrode of claim 1, the body further comprising at least one alignment feature selected from a slot or a notch formed extending inwardly from the exterior surface of the body between two of the segmented electrodes.

4. The pre-electrode of claim 1, the body further comprising at least one longitudinal step section formed in the exterior surface of the body along a longitudinal side of the body and extending from the distal end to the proximal end of the body.

5. The pre-electrode of claim 4, wherein the at least one longitudinal step section comprises a first longitudinal step section and a second longitudinal step section opposite the first longitudinal step section.

6. The pre-electrode of claim 1, wherein the at least one end wall step section comprises a first end wall step section formed in the exterior surface of the body on the distal end and a second end wall step section formed in the exterior surface of the body on the proximal end of the body.

7. The pre-electrode of claim 1 the body further comprising an annular groove.

8. A method of making a stimulation lead, the method comprising
   disposing the pre-electrode of claim 1 along a distal end portion of a lead body;
   forming a lead body around the pre-electrode; and
   removing the connecting material from the pre-electrode to release the segmented electrodes.

9. A pre-electrode for a stimulation lead, the pre-electrode comprising:
   a generally cylindrical body comprising an exterior surface, an interior surface opposite the exterior surface, a proximal end, and a distal end, the body comprising
      a plurality of segmented electrodes disposed around the body in a circumferentially spaced-apart configuration, each of the plurality of segmented electrodes having opposing side-walls extending between the proximal end and the distal end of the body,
      connecting material forming at least a portion of the exterior surface of the body, the connecting material coupling together the plurality of segmented electrodes, and
      at least one alignment feature selected from a slot or a notch extending inwardly from the exterior surface of the body between two of the segmented electrodes, wherein the at least one alignment feature extends through at least some of the connecting material that is located between at least two circumferentially-adjacent segmented electrodes.

10. The pre-electrode of claim 9, wherein the at least one alignment feature extends from the exterior surface of the body to the interior surface of the body.

11. The pre-electrode of claim 9, wherein the at least one alignment feature is a slot in the form of a groove extending from the proximal end to the distal end of the body and not extending to the interior surface of the body.

12. The pre-electrode of claim 9, where the at least one alignment feature comprises a first notch formed at the distal end of the body and a second notch formed at the proximal end of the body.

13. The pre-electrode of claim 9, the body further comprising an annular groove.

14. A method of making a stimulation lead, the method comprising
   disposing the pre-electrode of claim 9 along a distal end portion of a lead body;
   forming a lead body around the pre-electrode; and
   removing the connecting material from the pre-electrode to release the segmented electrodes.

15. A pre-electrode for a stimulation lead, the pre-electrode comprising:
   a generally cylindrical body comprising an exterior surface, a proximal end, and a distal end, the body comprising
      a plurality of segmented electrodes disposed around the body in a circumferentially spaced-apart configuration, each of the plurality of segmented electrodes having opposing side-walls extending between the proximal end and the distal end of the body,
      connecting material forming at least a portion of the exterior surface of the body, the connecting material coupling together the plurality of segmented electrodes, and
      at least one longitudinal step section formed in the exterior surface of the body along longitudinal side of the body and extending from the distal end to the proximal end of the body.

16. The pre-electrode of claim 15, the body further comprising at least one end wall step section formed in the exterior surface of the body on either the distal end or the proximal end of the body.

17. The pre-electrode of claim 15, wherein the at least one longitudinal step section comprises a first longitudinal step section and a second longitudinal step section opposite the first longitudinal step section.

18. The pre-electrode of claim 17, the body further comprising a first longitudinal region and a second longitudinal region, wherein the first and second longitudinal regions flank both the first longitudinal step section and the second longitudinal step section, and the first longitudinal region has an outer radius smaller than an outer radius of the second longitudinal region.

19. The pre-electrode of claim 17, the body further comprising a first longitudinal region and a second longitudinal region, wherein the first and second longitudinal regions flank both the first longitudinal step section and the second longitudinal step section, and the first longitudinal region and the second longitudinal region have a same outer radius.

20. A method of making a stimulation lead, the method comprising
- disposing the pre-electrode of claim 15 along a distal end portion of a lead body;
- forming a lead body around the pre-electrode; and
- removing the connecting material from the pre-electrode to release the segmented electrodes.

* * * * *